United States Patent [19]

Elerath

[11] Patent Number: 5,349,432
[45] Date of Patent: Sep. 20, 1994

[54] MULTI-LASER COHERENT IMAGING THROUGH ABERRATING MEDIA

[75] Inventor: Douglas E. Elerath, Alameda, N. Mex.

[73] Assignee: Hughes Aircraft Company, Los Angeles, Calif.

[21] Appl. No.: 989,264

[22] Filed: Dec. 11, 1992

[51] Int. Cl.$^5$ ............................................. G01J 1/00
[52] U.S. Cl. .................. 356/121; 250/201.9
[58] Field of Search ...................... 356/121; 250/201.9

[56] References Cited

U.S. PATENT DOCUMENTS 3,731,103  5/1973  O'Meara .................... 250/203.2
4,750,818  6/1989  Cochran ..................... 356/121

*Primary Examiner*—F. L. Evans
*Attorney, Agent, or Firm*—Hugh P. Gortler; M. W. Sales; W. K. Denson-Low

[57] ABSTRACT

An improved method for imaging laser illuminated objects through a near field aberrator, and/or for measuring the phase distortions of the aberrator. The method utilizes a set of at least three laser beams that are offset with respect to each other in a lateral direction. This offset produces three similarly offset but otherwise identical complex fields in the wave fronts of the reflected return at the sensors. The individual laser beams are tagged with identifying characteristics that are apparent at the sensors, whereby the reflected return may be identified and classified according to origin in individual laser beams. The sensor signals are processed to measure distortions in the aberrator and to apply the measurements to obtain an enhanced image.

19 Claims, 1 Drawing Sheet

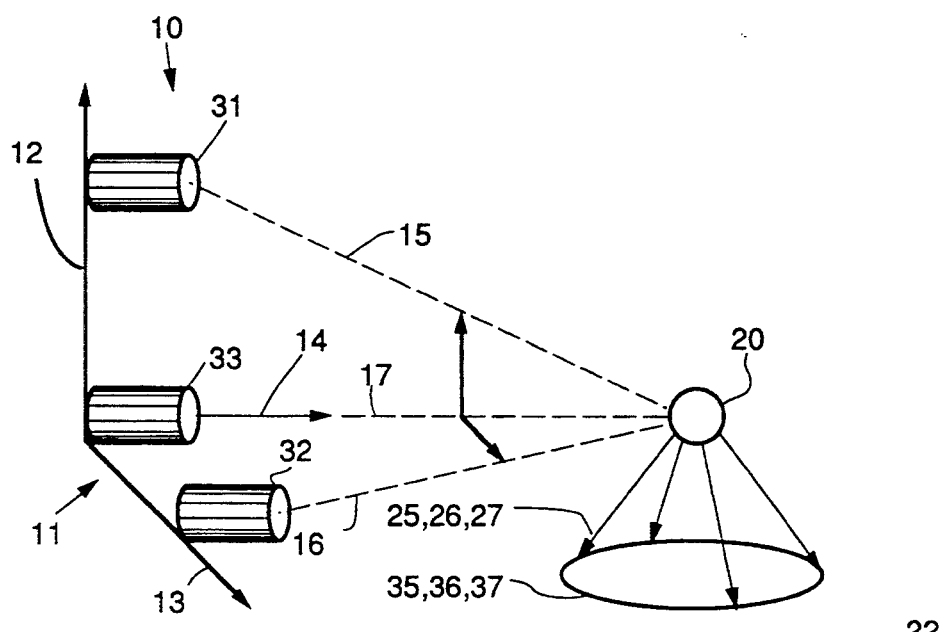
FIG. 1.
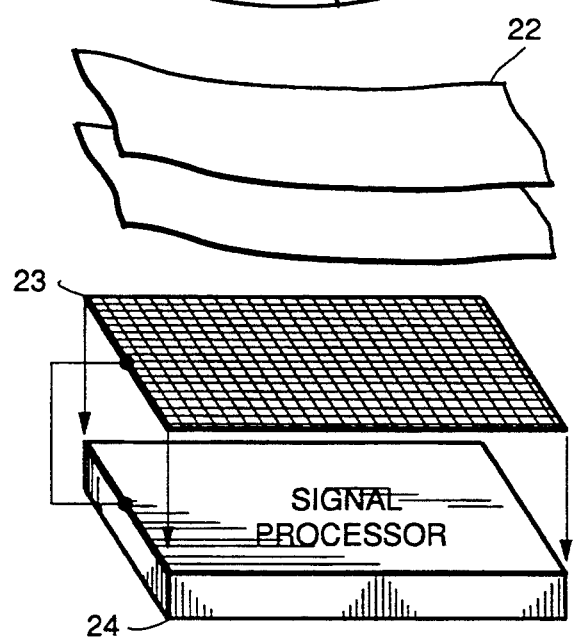
FIG. 2.
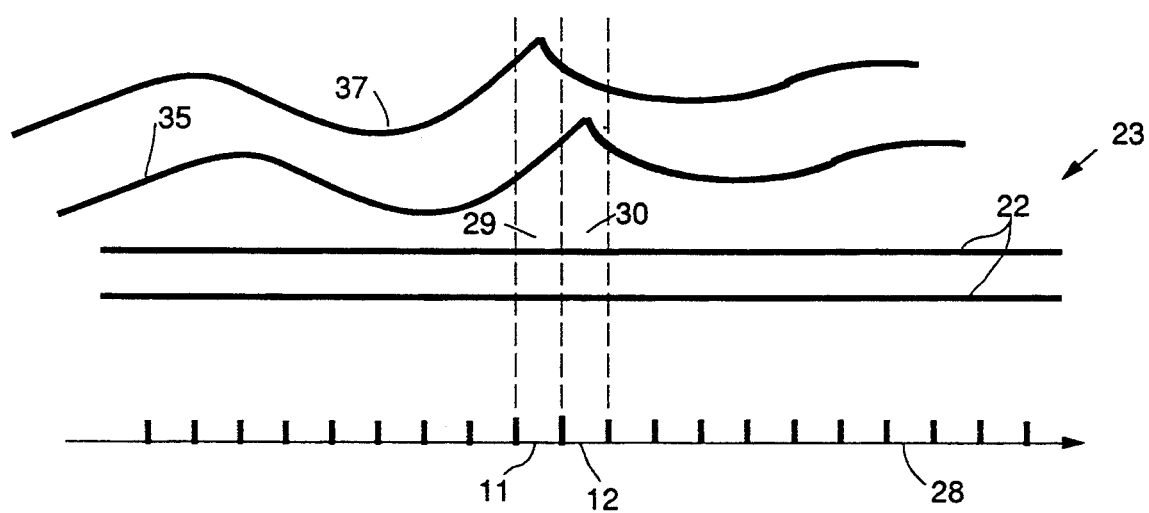

MULTI-LASER COHERENT IMAGING THROUGH ABERRATING MEDIA

BACKGROUND

The present invention relates to optical imaging technology and, more particularly, to measurement of and/or electronic compensation of optical phase distortion induced by an aberrating medium.

Optical signals may be significantly distorted as they pass through an aberrating medium such as the atmosphere. The phenomenon presents severe difficulties in achieving desired resolution in high quality optical imaging systems. The distortion generally takes the form of an aberration which can be represented locally as a tilt or slope of the wavefront of the received optical signal. Corrective compensation requires that either the local tilts due to the aberrating medium be measured and appropriate corrections be applied in the imaging process, or that the imaging process itself be rendered insensitive to the aberrations.

Heretofore, systems of direct measurement of the aberrations had the disadvantage of requiting the use of incoherent or unresolved sources. None of the techniques could use a coherent, extended source as the basis for measurements. In addition, prior measurement techniques are not inherently self referencing and require a known optical source. Prior imaging techniques which are insensitive to aberrations require either non-deterministic image sharpness algorithms, or the use of unwieldy and complex optical phase shifting means.

One conventional prior method of direct aberration measurement uses a Hartmann-type wavefront sensor to measure the local tilts of the wavefront. A basic Hartmann sensor has a detector array of individual photo-sensitive cells that sense the optical signal passing through a portion of the system aperture. That portion constitutes a subaperture that is focused by a lenslet array onto individual detector cells. Under ideal circumstances, the lenslets focus the subaperture portion of the incoming optical signal squarely on the center of the individual detector cells. However, the lenslets are sensitive to local tilts in the incoming wave front, and focus the imperfect signal off the center of respective detectors according to the tilt. This off center measurement is the indication of the local wavefront tilt. The total wavefront aberration can then be reconstructed by combining and processing these local tilt measurements. A serious difficulty in implementing this type of wavefront sensor lies in the nature of the off center determination. This requires an extremely accurate and stable mechanical alignment of the optical elements, and/or calibration scheme employing a local reference source. The alignment and calibration schemes are difficult in a practically realizable system.

A conventional method of performing imaging measurements which are insensitive to the presence of aberrations uses three laser beams illuminating an object of interest. The sources of the beams are separated by an amount Dx in the x direction and Dy in the y direction. The three beams are directed at a target. A resulting complex field pattern is produced by the three beams prior to passing through the aberrating medium. The field patterns of each of the three beams are spatially displaced, but are otherwise identical. The beams are mutually coherent, and thus create an interference pattern in the plane of a detector array. The processing of data at the detector array containing the interference pattern is essentially identical to that employed in the "4-bin" shearing interferometer algorithm developed by ITEK Corporation. In this case, the four distinct phases needed for processing at the detector array are created by pulse train forming optics at the laser end of the system.

Thus this system is implemented as a shearing wavefront slope sensor, so that the local wavefront slopes of the pattern at the detector array is measured. Since a shearing interferometer is a common path interferometer, the measurements at the detector may are insensitive to, and independent of, the aberrating medium. However, when this system is used, it is difficult to directly measure the intervening aberration. Furthermore, the system requires a complex beam division and phase delay system in order to provide the four distinct phases described above in the transmitted illuminator pulses.

Accordingly, it is an objective of the present invention to provide for direct measurement of intervening aberration in an imaging optical system. It is a further objective of the present invention to provide a system that does not require unreasonably stringent mechanical alignment of the optical elements. It is also an objective of the present invention to provide a system wherein either mutually coherent or mutually incoherent laser beams may be used to provide an imaging system that compensates for intervening aberrations as image enhancing corrections.

SUMMARY OF THE INVENTION

In accordance with these and other features and objectives of the present invention, there is provided an optical system in which an object is illuminated with multiple beams, and shifted but otherwise identical complex fields appear prior to the aberrating medium. The beams are individually tagged, and are therefore distinguishable at the sensor. They do not form a stationary interference pattern, and depending upon the type of sensor used, may be mutually incoherent. The tagging may comprise amplitude modulation of the beams, frequency modulation of the beams, frequency shifting of the beams, or any other technique which allows one to distinguish between the beams at the sensor. Depending upon the measurement sensor used, the beams may be beam-split off a single laser source, or may be provided by entirely separate lasers. However the beams must be close enough in frequency so as to produce nearly identical but shifted speckle fields prior to the aberrating medium. Such an arrangement provides a "look ahead" capability that is used to determine the aberration of an intervening medium, and/or to determine the complex field which would have been measured in the absence of an aberrating medium.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which:

FIG. 1 shows a three dimensional schematic representation of a multi-laser imaging system in accordance with the principles of the present invention; and FIG. 2 shows complex optical wavefront fields approaching sensor means through an aberrating medium.

DETAILED DESCRIPTION

Referring now to FIG. 1, there is shown a schematic representation of a multilaser imaging system 10 according to the principles of the present invention. To the left in FIG. 1 is shown a three dimensional, orthogonal coordinate system 11 having an x-axis 12, a y-axis 13 and a z-axis 14. This coordinate system 11 represents means for supporting the sources of first, second and third laser beams 15, 16, 17 that emanate substantially from the origin of the axes system 11 and point substantially along the Z-axis 14. In FIG. 1 the third laser beam 17 is referenced at the origin of the coordinate system 11 and pointed along the z-axis 14. The remaining two laser beams 15, 16 are also referenced substantially at the origin of the coordinate system 11 but are displaced a fractional linear distance from the origin along the x-axis 12 and the y-axis 13, respectively. These two beams 15, 16 are also pointed at the same target object 20 as beam 17, and are consequently tilted at a slight angle with respect to the z axis 14. As depicted in FIG. 1, the first beam 15 lies in the x-z plane with a small negative x component of tilt, and the second beam 16 lies in the y-z plane with a small negative y component of tilt. This fractional tilt results in a fractional linear displacement in the plane of the sensor as will be described below. The coordinate system 11 of FIG. 1 has means (not shown) permitting pointing of the coordinate system 11, and thus of the set of laser beams 15, 16, 17 at a target object 20 chosen for investigation.

The laser beams 15, 16, 17 are provided by first, second and third lasers 31, 32, 33, respectively. These lasers 31, 32, 33 may comprise three separate lasers or may comprise a single laser employing a beamsplitter to form the three laser beams 15, 16, 17. Additionally, the lasers 31, 32, 33 provide identification means for tagging the three laser beams 15, 16, 17. The tagging injects additional laser signal components that may comprise amplitude modulation, frequency modulation or frequency shifting of the laser beams 15, 16, 17. Any other tagging technique may be employed which permits distinguishing between the laser beams 15, 16, 17.

In FIG. 1 there is also shown a sensor 23 as pan of the overall imaging system 10. The sensor 23 may include an array of individual detector cells wherein the center to center distance between individual detector cells is adapted to substantially correspond to the fractional displacement between the received complex fields. The sensor 23 may be a complex field or wavefront slope sensor such as a Hartmann sensor, an optical wavefront sensing system, a shearing interferometer, an electronic phased array or any other heterodyne or homodyne system. The sensor 23 is connected to a signal processor 24 that is adapted to extract the signal components arising from the tagging of the first, second and third laser beams 15, 16, 17 and thus to distinguish between the laser beams 15, 16, 17 based on measurements of their identification or tagging parameters. Also shown in FIG. 1 is the target object 20 illuminated by the laser beams 15, 16, 17. An aberrating medium 22 is shown between the target object 20 and the sensor 23. The aberrating medium 22 may comprise the atmosphere or any similar wavefront distorting medium.

In operation, the laser beams 15, 16, 17, illuminate the object 20 thus producing corresponding reflected signals 25, 26, 27 from the target object 20. The first, second and third laser beams 15, 16, 17, produce corresponding first, second and third reflected signals 25, 26, 27, respectively resulting in first, second and third identical complex fields 35, 36, 37 prior to the aberrating medium 22. However, because the sources of the laser beams 15, 16, 17 are shifted with respect to each other, the complex fields 35, 36, 37 associated with each of the laser beams 15, 16, 17 are shifted proportionally. If the sensor and laser source are located at ranges $r_1$ and $r_2$ respectively from the target object 20, then the displacement between the received fields is $r_1/r_2$.

In the absence of the aberrating medium 22, all of the complex fields 35, 36, 37 are presented to the sensor 23. When, for example, the third and first laser beams 17, 15 are shifted by the amount of the center to center distance of the detector cells in the array of individual detector cells, then the third laser beam 17 presents a corresponding third complex field 37 to an arbitrary detector $i_1$ and the first laser beam 15 presents its corresponding first complex field 35 to an adjacent detector $i_2$ located in the direction of the x-axis 12 of the coordinate system 11. Because the third and first complex fields 37, 35 are identical, the tagged detector signal measured in detector $i_1$ corresponding to the third laser beam 17 is equal to the tagged detector signal measured in detector $i_2$ corresponding to the first laser beam 15. However, in the presence of an aberrating medium 22, the two measurements may not be equal. Then, any difference in the two detector measurements is due to the aberrating medium 22 and is a measure of the distortion presented by the aberrating medium 22. This is explained more fully by referring to FIG. 2.

Referring now to FIG. 2, there is shown a one dimensional representation of the laser complex fields 37, 35 appearing relative to the aberrating medium 22 and to the sensor 23. The sensor 23, has a horizontal axis 28 that represents a linear distance of the detector array, the tic marks represent the individual detectors of the detector array. The detector cells $i_1$ and $i_2$ are arbitrary detector cells from among the detector array of the sensor 23 and chosen to illustrate the principle of this invention. The vertical columns represent fast and second subapertures 29 and 30 corresponding respectively to effective apertures of detector cells $i_1$ and $i_2$. The upper graphs are one dimensional representations of the third and first complex fields 37 and 35 respectively, and are shown displaced relative to one another by the center to center distance between the detector cells. The aberrating medium 22 is shown positioned between the third and first complex fields 37, 35 and the sensor 23.

FIG. 2 shows that the local wavefront slope of the third complex field 37 of the third laser beam 17 that falls within the first subaperture 29 of detector cell $i_1$ is equal to the local wavefront slope of the fast complex field 35 of the first laser beam 15 that falls within the second subaperture 30 of detector cell $i_2$ prior to the aberrating medium 22. Absent the aberrating medium 22, the third laser beam 17 presents the same field to detector $i_1$ as does the first laser beam 15 to detector $i_2$. In general, in this one dimensional example, the third laser beam 17 presents the same field to the $i^{th}$ detector as will the first laser beam 15 to the $(i+1)$st detector. However, it is necessary to take into account the presence of a "thin" aberrating medium 22 in the near field of the sensor means 23. Since the detectors are small relative to the structure of both the aberrating medium 22 and the third and first complex fields 37, 35 reflected from the target object 20, then the third and first complex fields 37, 35 sensed by any one given detector may be defined to be correct.

The measurements of the rest of the detectors may now be referenced to that one measurement. In FIG. 1 the field as sensed by the detector $i_1$ is defined to be correct. Then, the failure of the first complex field 35 as sensed by detector $i_2$ to look just like the third complex field 37 as measured by detector $i_1$ is due strictly to the intervening aberrating medium 22. Since the detectors are small relative to the structure of the aberrating medium 22, this error can be represented as a tilt, and therefore the measurement of the fast laser beam 15 in detector $i_2$ can be corrected. Since both laser beams 17 and 15, as sensed in detector $i_2$, have passed through the same aberrating medium 22, this correction to the first laser beam 15 also corrects the third laser beam 17. Inductively, the measurement of the third laser beam 17 in detector i may be used to correct the measurement of the first laser beam ! 5, and perforce the third laser beam 17, in detector $i+1$. This not only results in the correct measurements in each of the detectors, but also results in the corrections providing a measure of the aberrating medium 22.

A correction procedure entirely analogous to the one given above may be followed in a two dimensional case by repeating the iterative procedure in each of the two dimensions. Since the starting detector cell is arbitrary, and since there are many distinct paths between any two detectors within the sensor, the sequential correction procedure described above may be better described by an over determined set of algebraic equations, which are solved in a least squares sense to determine a noise optimal estimate for both the field and for the aberrations.

Thus there has been described a new and improved multi-laser imaging system that allows an extended laser illuminated object to be imaged through a near field aberrator, and/or to allow the phase distortions of the aberrator to be measured directly. The system is deterministic and does not require iterative algorithmic processing. It is entirely self referencing, and does not require a known point source, or a set of sources, between the aberrator and the object, or in the far field of the imaging system, to be used as a reference. It allows simultaneous measurement of the aberrator and imaging of the object without use of deformable optics. It allows a variety of different wavefront sensing techniques to be used in measuring the received dam. It may be used for either real time image compensation with deformable optics or for computer based imaging. Also, it allows the illuminator lasers to be either mutually coherent but shifted from one another, or be mutually incoherent.

It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. A method of determining phase distortions induced by a near field aberrator in an active laser system, said method comprising the steps of:

forming a plurality of laser beams having known characteristic signals, and pointing the laser beams at a common object that generate laser return signals from illuminated target objects;

maintaining spatial displacement of the laser beams with respect to each other in an orthogonal coordinate system including the axis of one reference laser beam;

incorporating a distinguishable identification signature signal imbedded in the characteristic signal of each laser beam;

using an array of detectors responsive to the laser characteristic signals to provide detector output signals representing return signals from the target objects, wherein center to center spacings between individual detectors is substantially equal to the spatial displacement of the axes of the laser beams times the ratio of a return path range divided by a transmit path range;

extracting the laser return signals according to their identification signature signal from each detector output signal and classifying each return signal according to it's origin among the plurality of laser beams; and comparing the return signals from each detector respecting each laser beam thereby determining the aberrator induced phase distortion.

2. The method for determining phase distortions according to claim 1 wherein the step of forming a plurality of laser beams comprises forming the beams by utilizing a corresponding plurality of individual lasers.

3. The method for determining phase distortions according to claim 2 wherein the step of incorporating an identification signature signal comprises utilizing diverse frequencies in the individual lasers characteristic signals.

4. The method for determining phase distortions according to claim 2 wherein the step of incorporating an identification signature signal comprises utilizing diverse amplitude modulation on the plurality of laser characteristic signals.

5. The method for determining phase distortions according to claim 2 wherein the step of incorporating an identification signature signal comprises utilizing a relative shift in the frequencies of the respective laser characteristic signals.

6. The method for determining phase distortions according to claim 2 wherein the step of incorporating an identification signature signal comprises using three pulsed lasers fired at different times.

7. The method for determining phase distortions according to claim 1 wherein the step of forming a plurality of laser beams comprises forming plurality of laser beams by utilizing a single laser and a plurality of beamsplitters and reflecting mirrors.

8. The method for determining phase distortions according to claim 6 wherein the step of incorporating a distinguishable identification signature signal comprises interposing characteristic signal modifiers in the beam path of each laser beam.

9. The method for determining phase distortions according to claim 1 wherein return complex fields are determined by measuring the local slope of the return wavefronts.

10. An optical imaging system for imaging laser-illuminated objects through an aberrating medium, said system comprising:

platform means for illuminating an object, said platform means including laser means for pointing a plurality of laser beams at the object, said beams being spatially displaced with respect to each other in an orthogonal coordinate system; and tagging means for embedding identifying components in the laser beams; and a plurality of detectors adapted to receive the laser beams reflected by the object, said detectors being arranged in a two-dimensional array having a center-to-center detector spacing substantially equal to the spatial displacement of the laser beams or to fractions of the spatial displacements.

11. The optical imaging system according to claim 10 wherein the plurality of laser beams comprise beams formed by utilizing a corresponding plurality of individual lasers.

12. The optical imaging system according to claim 11 wherein the tagging means comprises means for imbedding diverse frequencies in the individual lasers characteristic signals.

13. The optical imaging system according to claim 11 wherein the tagging means comprises means for imbedding diverse amplitude modulation on the plurality of laser characteristic signals.

14. The optical imaging system according to claim 11 wherein the tagging means comprises means for imbedding a relative shift in the frequencies of the respective laser characteristic signals.

15. The optical imaging system according to claim 10 wherein the tagging means comprises pulsed lasers fired at different times.

16. The optical imaging system according to claim 10 wherein the laser means comprises a single laser and a plurality of beamsplitters and reflecting mirrors for pointing the plurality of laser beams.

17. The optical imaging system according to claim 16 wherein the tagging means comprises means for interposing characteristic signal modifiers in a beam path of each laser beam.

18. The optical imaging system according to claim 10 further comprising processing means, responsive to detector output signals from said plurality of detectors, for processing the detector output signals to provide signals indicative of aberration of the aberrating medium.

19. The optical imaging system according to claim 18 wherein the processing means comprises means for measuring the slope of the return wavefronts to determine the return complex fields.

* * * * *